United States Patent
Suwald et al.

(10) Patent No.: US 9,772,283 B2
(45) Date of Patent: Sep. 26, 2017

(54) IDENTIFICATION OF ASSETS

(71) Applicant: NXP B.V., Eindhoven (NL)

(72) Inventors: Thomas Suwald, Hamburg (DE); Arne Burghardt, Hamburg (DE)

(73) Assignee: NXP B.V., Eindhoven (NL)

( * ) Notice: Subject to any disclaimer, the term of this patent is extended or adjusted under 35 U.S.C. 154(b) by 174 days.

(21) Appl. No.: 14/708,067

(22) Filed: May 8, 2015

(65) Prior Publication Data

US 2015/0346094 A1    Dec. 3, 2015

(30) Foreign Application Priority Data

May 30, 2014    (EP) ..................................... 14170629

(51) Int. Cl.
*G01N 21/62*    (2006.01)
*G01N 27/00*    (2006.01)
*G01N 29/34*    (2006.01)
*G06F 21/73*    (2013.01)

(52) U.S. Cl.
CPC ............ *G01N 21/62* (2013.01); *G01N 27/00* (2013.01); *G01N 29/34* (2013.01); *G06F 21/73* (2013.01)

(58) Field of Classification Search
CPC ........ G01N 21/62; G01N 27/00; G01N 29/34; G01N 2291/015
USPC ........................................ 73/865.8, 599, 600
See application file for complete search history.

(56) References Cited

U.S. PATENT DOCUMENTS 5,969,260 A * 10/1999 Belk ........................ G01B 7/16
                                                         73/773
2010/0256928 A1* 10/2010 Larose ................. G01N 29/069
                                                         702/39

FOREIGN PATENT DOCUMENTS

WO    2012/122994 A1    9/2012

OTHER PUBLICATIONS

Extended European Search Report for EP Patent Appln. No. 14175992.8 (dated Oct. 30, 2014).

* cited by examiner

*Primary Examiner* — David M Gray
*Assistant Examiner* — Andrew V Do
(74) *Attorney, Agent, or Firm* — Rajeev Madnawat

(57) ABSTRACT

There is described a device for identifying an asset. The device comprises (a) a piece of material having predetermined physical properties, the piece of material being adapted to be irreversibly attached to the asset, (b) a stimulation and measurement unit attached to the piece of material, the stimulation and measurement unit being adapted to apply a predetermined stimulation to the piece of material and to measure a corresponding response from the piece of material, (c) an analysis unit adapted to analyze the measured response from the piece of material, and (d) a communication unit adapted to output data representative of the analysis of the measured response. There is also described an asset, an identification system and a method of identifying an asset. Furthermore, there is described a computer program.

15 Claims, 7 Drawing Sheets

IDENTIFICATION OF ASSETS

CROSS-REFERENCE TO RELATED APPLICATIONS

This application claims the priority under 35 U.S.C. §119 of European patent application no. 14170629.1, filed on May 30, 2014, the contents of which are incorporated by reference herein.

FIELD OF THE INVENTION

The present invention relates to the field of identification of assets, in particular to a device for identifying an asset, an asset comprising such a device, an identification system, a method of identifying an asset, and a computer program.

BACKGROUND

In an electronically connected world there is a desire to identify valuable assets or items such as devices, vehicles and production equipment and more by electronic means.

It is common to apply e.g. identification numbers or serial numbers as impact numbers. These impact numbers become part of the item and may be used for optical identification. One example is chassis numbers of vehicles. These identification numbers are also stored by some manufacturers in electronically readable storage devices that are attached to the item. However, it is difficult to prove that the storage device is actually the authentic storage device belonging to the item to be identified. By exchanging the storage device, the item to be identified may receive a completely different electronic identity. This may result in a change of ownership or a change of the item's value or a change of accessible features.

There may thus be a need for an improved way of electronically identifying valuable items.

SUMMARY

This need may be met by the subject matter according to the independent claims. Advantageous embodiments of the present invention are set forth in the dependent claims.

According to a first aspect of the invention, there is provided a device for identifying an asset. The device comprises (a) a piece of material having predetermined physical properties, the piece of material being adapted to be irreversibly attached to the asset, (b) a stimulation and measurement unit attached to the piece of material, the stimulation and measurement unit being adapted to apply a predetermined stimulation, to the piece of material and to measure a corresponding response from the piece of material, (c) an analysis unit adapted to analyze the measured response from the piece of material, and (d) a communication unit adapted to output data representative of the analysis of the measured response.

This aspect is based on the idea that a piece of material having predetermined physical properties and capable of being irreversibly attached to the asset, i.e. as an integral part of the asset, is subjected to a predetermined stimulation. The corresponding response, which is determined by the specific physical properties of the piece of material and the stimulation, is measured and analyzed, and data representative of the analysis is output through a communication unit. In other words, the unique combination of physical properties and stimulation provides a unique root identity for the asset when the piece of material is irreversibly attached.

In the present context, the term "irreversibly attached" may particularly denote that the piece of material is attached to the asset is such a manner that it cannot be removed without damaging the piece of material and/or the asset. In particular, the piece of material may be irreversibly attached by welding, gluing, laminating or another similar process.

In the present context, the term "predetermined physical properties" may particularly denote acoustical, optical or electrical properties.

The piece of material may comprise metal, such as cast iron, composite material or a combination thereof. In particular, the predetermined physical properties of the material may be caused by production specific material irregularities, such as random processing variations or deliberate processing of the material. The tatter may involve laser based processing, forging and tempering steps.

In the present context, the term "apply a predetermined stimulation" may particularly denote that the piece of material is exhibited to a certain physical influence.

In the present context, the term "corresponding response from the piece of material" may particularly denote a reaction in or from the material caused by the stimulation.

The analysis performed by the analysis unit may in particular involve determination of a set of characteristic features of the response, such as characteristic features relating to a time response or a frequency response. The characteristic features may provide a "fingerprint" characteristic of the combination of material and stimulation. Data representing such a "fingerprint" may be processed in a similar way, e.g. by pattern matching, as it is known in the field of biometric systems in order to determine identity and/or authenticity of the asset.

The communication unit is preferably a data interface capable of communicating with an external system that aims at determining the identity of the asset or at verifying the authenticity of the asset. The communication unit may be designed to perform wired or wireless communication with such an external system, either directly or through an internal communication system or bus of the asset.

According to an embodiment, the device further comprises (a) a memory unit for storing an expected response corresponding to the predetermined stimulation, wherein (b) the analysis unit is adapted to determine whether the measured response from the piece of material corresponds to the expected response, and wherein (c) the communication unit is adapted to output data indicative of whether the measured response from the piece of material corresponds to the expected response.

The expected response may be obtained and stored in the memory unit during a training process, which may be conducted during manufacture of the asset. The data representing the expected response may be stored in a secure manner, e.g. in encrypted form, in the memory unit in order to maintain the integrity of the system.

The data indicative of whether the measured response from the piece of material corresponds to the expected response may comprises a simple "yes" or "no" or it may comprise a score or percentage indicating a degree of correspondence between measured and expected response.

According to a further embodiment, the communication unit is adapted to output data representative of the measured response and/or of the expected response.

In other words, the communication unit outputs data representing the measured "fingerprint" of the device and/or the expected "fingerprint" of the device. Both "fingerprints" may preferably be represented by a set of characteristic feature values as discussed above.

Upon receiving the data, an external system may use it to determine the identity of the asset and to verify the authenticity of the identity.

According to a further embodiment, the device further comprises a cryptographic unit adapted to decrypt an encrypted request for identification received by the communication unit and to encrypt data output by the communication unit.

In other words, the cryptographic unit assures that communication with external systems take place in a secure manner. In particular, only external systems that have access to the necessary cryptographic keys are able to communicate with the device.

The cryptographic unit may furthermore be responsible for maintaining security of the data representing the expected response that is stored in the memory unit as discussed above.

According to a further embodiment, the stimulation and measurement unit comprises a plurality of stimulation elements and a plurality of measurement elements.

The stimulation elements and measurement elements are preferably arranged at individual positions, e.g. in a matrix structure, on one or more surfaces of the piece of material. Thereby, the stimulation may take place at several different positions and the measurement may similarly take place at various positions. Accordingly, the "predetermined stimulation" may comprise a variety of stimulation patterns and the measurement may similarly be performed in accordance with a variety of measurement patterns. Each combination of stimulation pattern and measurement pattern provides a specific "fingerprint". Furthermore, the asset's "fingerprint" may be obtained by combining a series of stimulation and measurement patterns. In the latter case, the use of several combinations of patterns may improve the uniqueness of the "fingerprint".

According to a further embodiment, (a) the stimulation elements are selected from the group consisting of acoustical stimulators, optical stimulators and electrical stimulators, and (b) the measurement elements are correspondingly selected from the group consisting of acoustical sensors, optical sensors and electrical sensors.

In the present context, the term "acoustical stimulator" may in particular denote a device capable of stimulating the piece of material by coupling acoustical energy into the material, such as a loudspeaker or a transducer. Similarly, the term "acoustical sensor" may denote a microphone or transducer capable of measuring a resulting acoustic signal at a certain position of the piece of material.

In the present context, the term "optical stimulator" may in particular denote a device capable of stimulating the piece of material by coupling optical energy into the material, such as an LED or similar light source. Similarly, the term "optical sensor" may denote a photo sensor or similar sensor capable of measuring a resulting optical signal at a certain position of the piece of material.

In the present context, the term "electrical stimulator" may in particular denote a device capable of stimulating the piece of material by coupling electrical energy into the material, such as a current or voltage source. Similarly, the term "electrical sensor" may denote a device capable of measuring a resulting electrical signal at a certain position of the piece of material, e.g. in order to determine a resistance.

According to a further embodiment, the stimulation elements comprise ultrasonic transducers for applying an ultrasonic stimulation to the piece of material, and wherein the measurement elements comprise ultrasonic transducers for measuring an ultrasonic response from the piece of material.

It is noted that the device may comprise ultrasonic transducers which may be selectively used for stimulation and measurement. Alternatively, some ultrasonic transducers may be dedicated to stimulation and other ultrasonic transducers may be dedicated to measurement.

The ultrasonic transducers may be narrow band transducers or wide band transducers. In particular, the ultrasonic transducers may be piezoelectric transducers capable of operating within a frequency range from about 20 kHz to 1 MHz.

According to a further embodiment, the communication unit is adapted to receive a request for identification, the request for identification comprising a challenge identifying at least one of the plurality of stimulation elements and at least one of the plurality of measurement elements, and the stimulation and measurement unit is adapted to apply the predetermined stimulation in accordance with the challenge by activating the at least one stimulation element identified by the challenge and to measure the corresponding response at the at least one measurement element identified by the challenge.

In other words, the system issuing a request for identification transmits a challenge in the form of a pattern defining the stimulation element(s) and measurement element(s) that are to be used in the identification process. The transmission of the request including the challenge is preferably encrypted as discussed above. Upon decryption of the challenge, the stimulation and measurement unit applies the stimulation by activating the selected stimulation elements and performs the corresponding measurement at the selected measurement elements.

According to a further embodiment, the stimulation and measurement unit is adapted to apply the predetermined stimulation as a signal having a predetermined frequency.

The predetermined frequency may be selected in accordance with a predefined scheme stored in the memory unit. For example, the stimulation may take place with a 40 kHz ultrasound signal output by one or more transducers, either simultaneously or in dedicated time slots. In another example, several stimulations may be performed, e.g. one at 40 kHz, another one at 80 kHz, and a third one at 120 kHz.

By varying the frequency, a further multiplicity of "fingerprints" of one single device may be obtained.

By stimulating and measuring a number of these "fingerprints", i.e. with various stimulation and measurement patterns and various frequencies, it is possible to obtain a low False Acceptance Rate (FAR) and a high False Reject Rate (ERR).

According to a second aspect, there is provided an asset comprising a device according to the first aspect or any of the above embodiments, wherein the piece of material is an integral part of the asset.

This aspect is essentially based on the same idea as the first aspect discussed above, i.e. that a unique combination of physical properties and stimulation provides a unique root identity for the asset when the piece of material is irreversibly attached as an integral part of the asset.

The piece of material may be made an integral part of the asset by welding, gluing, laminating, etc. and is thus "irreversibly attached to the asset. For example, the piece of material may comprise a piece of cast iron welded onto a part of the engine block in an automotive vehicle.

As the physical characteristics of the piece of material is influenced by the fastening process, it is virtually impossible to remove the device from an asset and replace it with another one in order to provide the asset with a faked identity.

According to a third aspect, there is provided an identification system comprising (a) an asset according to the second aspect, and (b) a service device in data communication with the communication unit, wherein the service device is adapted to transmit a request for identification to the communication unit and to receive data representative of the analysis of the measured response from the communication unit.

This aspect is based on essentially the same idea as the first and second aspects and various embodiments discussed above. In particular, it allows the service device to obtain an identification of the asset and/or to verify the authenticity of the identification.

According to an embodiment, the service device comprises or is in data communication with an identification database, and the service device is adapted to identify the asset by querying the identification database based on the received data that is representative of the analysis of the measured response from the communication unit.

In other words, the service device may use the identification database to obtain an ID (such as a vehicle identification number) corresponding to the "fingerprint" of the asset.

According to a fourth aspect, there is provided a method of identifying an asset to which a piece of material having predetermined physical properties is attached, the method comprising (a) applying a predetermined stimulation to the piece of material, (b) measuring a response from the piece of material corresponding to the predetermined stimulation, (c) analyzing the measured response from the piece of material, and (d) outputting data representative of the analysis of the measured response.

The method may preferably be implemented in a device according to the first aspect and any of the embodiments thereof as described above.

According to an embodiment, the method further comprises identifying the asset based on the data representative of the analysis of the measured response.

The actual identification of the asset may take place in the device attached to the asset or in an external device, such as a service device, connected to the asset device.

According to fifth aspect, there is provided a computer program comprising computer executable instructions which, when executed by a computer, causes the computer to perform the steps of the method according to the third aspect.

According to a sixth aspect, there is provided a computer program product comprising a computer readable data carrier loaded with a computer program according to the fifth aspect.

It should be noted that embodiments of the invention have been described with reference to different subject matters, in particular, some embodiments have been described with reference to method type claims whereas other embodiments have been described with reference to apparatus type claims. However, a person skilled in the art will gather from the above and the following description that, unless otherwise indicated, in addition to any combination of features belonging to one type of subject matter also any combination features relating to different subject matters, in particular a combination of features of the method type claims and features of the apparatus type claims, is also disclosed with this document.

The aspects defined above and further aspects of the present invention will be apparent from the examples of embodiment to be described hereinafter and are explained with reference to the examples of embodiment. The invention will be described in more detail hereinafter with reference to examples of embodiment to which the invention is, however, not limited.

DETAILED DESCRIPTION

Figure 1:
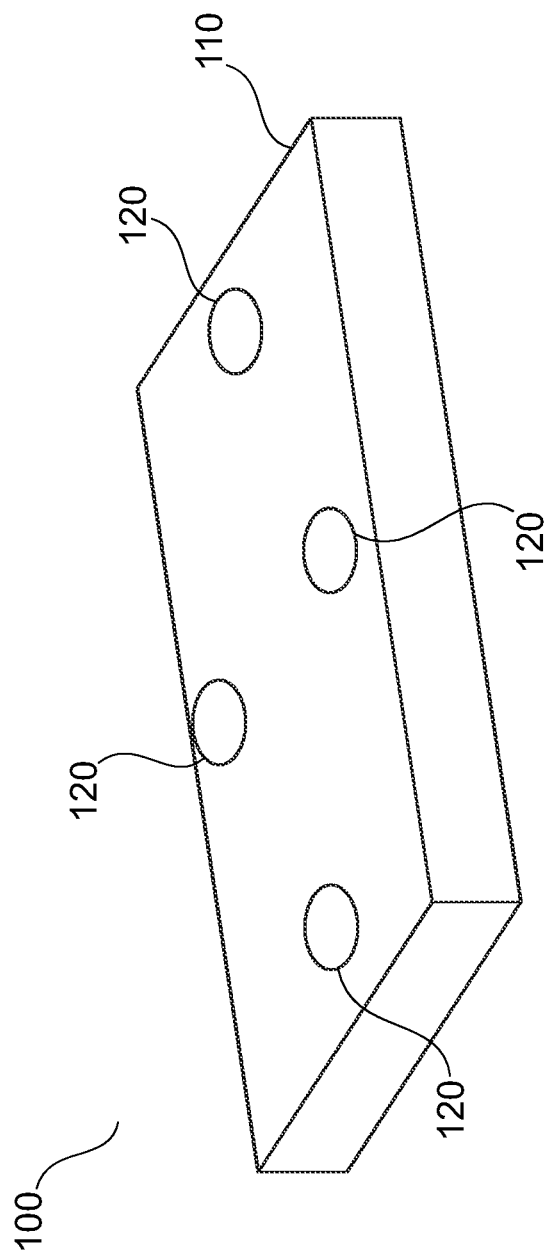
FIG. 1 shows a device according to an embodiment of the present invention.

The illustration in the drawing is schematic. It is noted that in different figures, similar or identical elements are provided with the same reference signs or with reference signs, which differ only within the first digit.

FIG. 1 shows a device 100 according to an embodiment of the present invention. More specifically, the device 100 comprises a flat rectangular piece 110 of material having predetermined physical properties, and four ultrasonic transducers 120 arranged on the upper surface of the piece 110. The flat rectangular piece 110 of material may e.g. be a piece of cast iron which has been processed (laser based processing, forging, and tempering steps) in order to exhibit individual physical properties as described further below in connection with FIG. 3.

Figure 2:
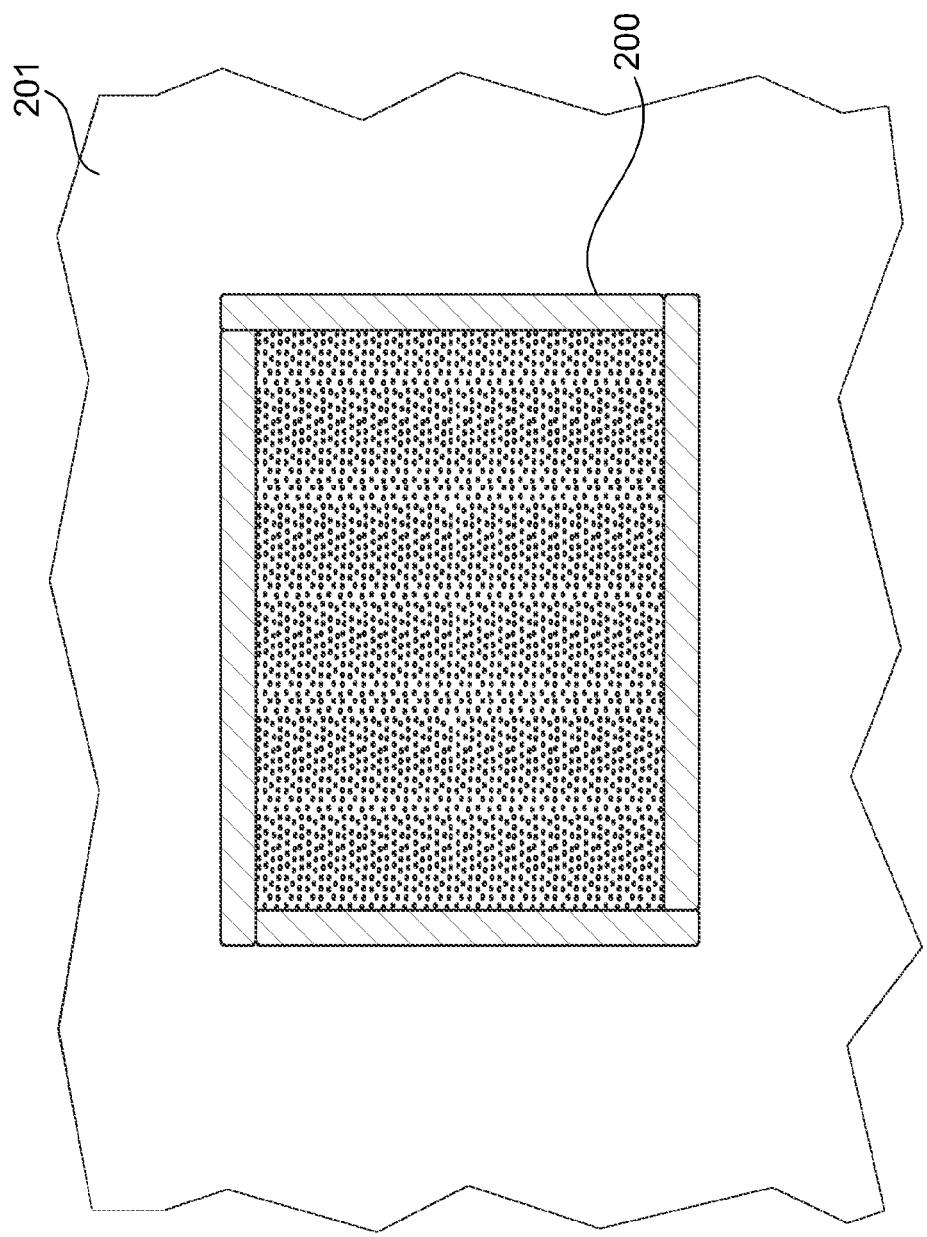
FIG. 2 shows a device attached to an asset in accordance with an embodiment of the present invention.

FIG. 2 shows a device 200 attached to an asset in accordance with an embodiment of the present invention. More specifically, the device 200 is welded, glued or otherwise irreversibly attached to a surface 201 of the asset. The surface 201 may e.g. be the surface of a motor block or another essential substantially non-removable part in an automotive vehicle.

Figure 3:
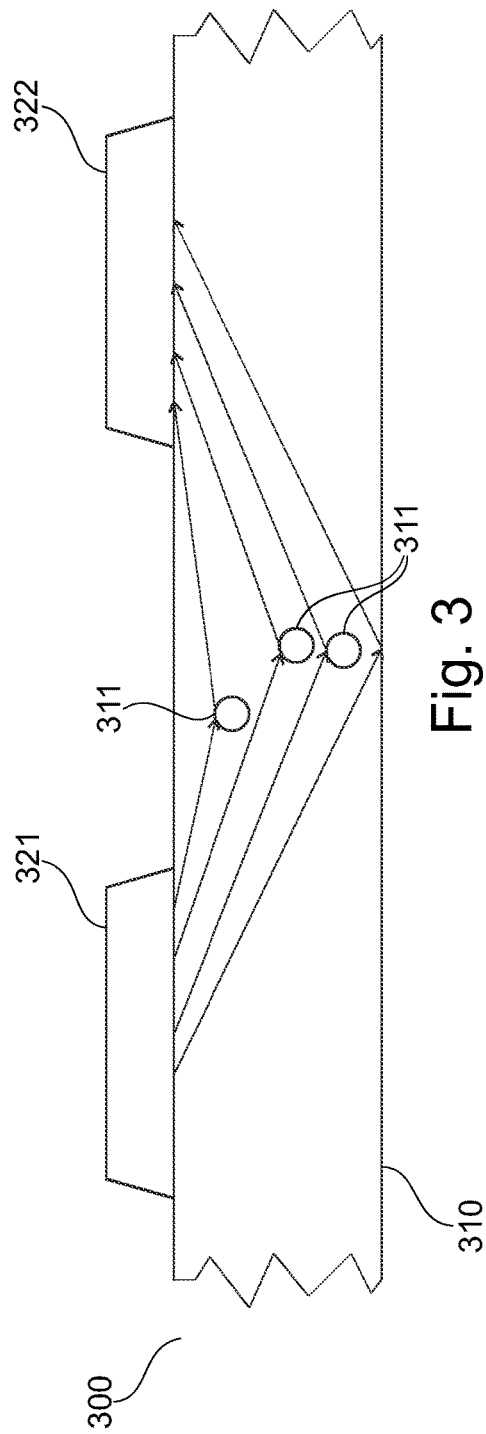
FIG. 3 shows the functional principle of a device according to an embodiment of the present invention.

FIG. 3 shows the functional principle of a device 300 according to an embodiment of the present invention. The device 300 comprises a flat piece of cast iron 310 which is shown from the side. The cast iron has been processed and welded to a surface of an asset (not shown) such that it contains several randomly distributed material irregularities, such as air bubbles 311. An ultrasonic transmitting transducer 321 and an ultrasonic receiving transducer 322 are attached to the upper surface of the piece 310. The transducers 321 and 322 are piezo-ceramic transducers and although they are respectively designated as transmitter and receiver, they are both capable of acting as transmitting and receiving transducers.

In operation, the transmitting transducer 321 injects an ultrasonic signal with a frequency of e.g. 40 kHz into the piece 310. The ultrasonic signal is reflected at the material irregularities 311 and a the opposite surface of the piece 310 such that the receiving transducer 322 receives a number of corresponding signal peaks at different points in time (corresponding to the length of the propagation path between the transducers 321 and 322).

Figure 4:
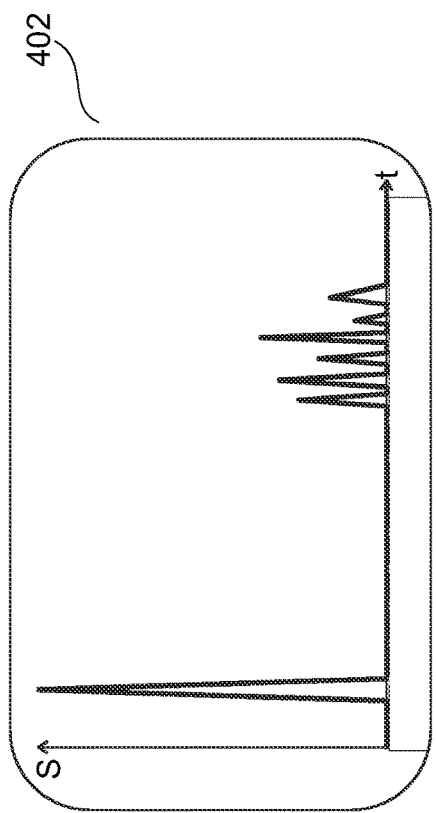
FIG. 4 is a graph showing a measured response caused by a stimulation of a device in accordance with an embodiment of the present invention.

FIG. 4 is a graph 402 showing a measured response caused by a stimulation of a device in accordance with an embodiment of the present invention. More specifically, the graph 402 shows the signal amplitudes at the receiving transducer 322 shown in FIG. 3 as a function of time t. The graph 402 is an example of an ultrasonic "fingerprint" of the device 300.

Returning to FIG. 3, it is noted that the device 300 may contain only one transducer acting as both transmitter and receiver or the device 300 may comprise more than two transducers which can be individually selected to act respectively as transmitter(s) and receiver(s). In the latter case, it becomes possible to apply a variety of different stimulation patterns resulting in correspondingly different ultrasonic "fingerprints".

Figure 5:
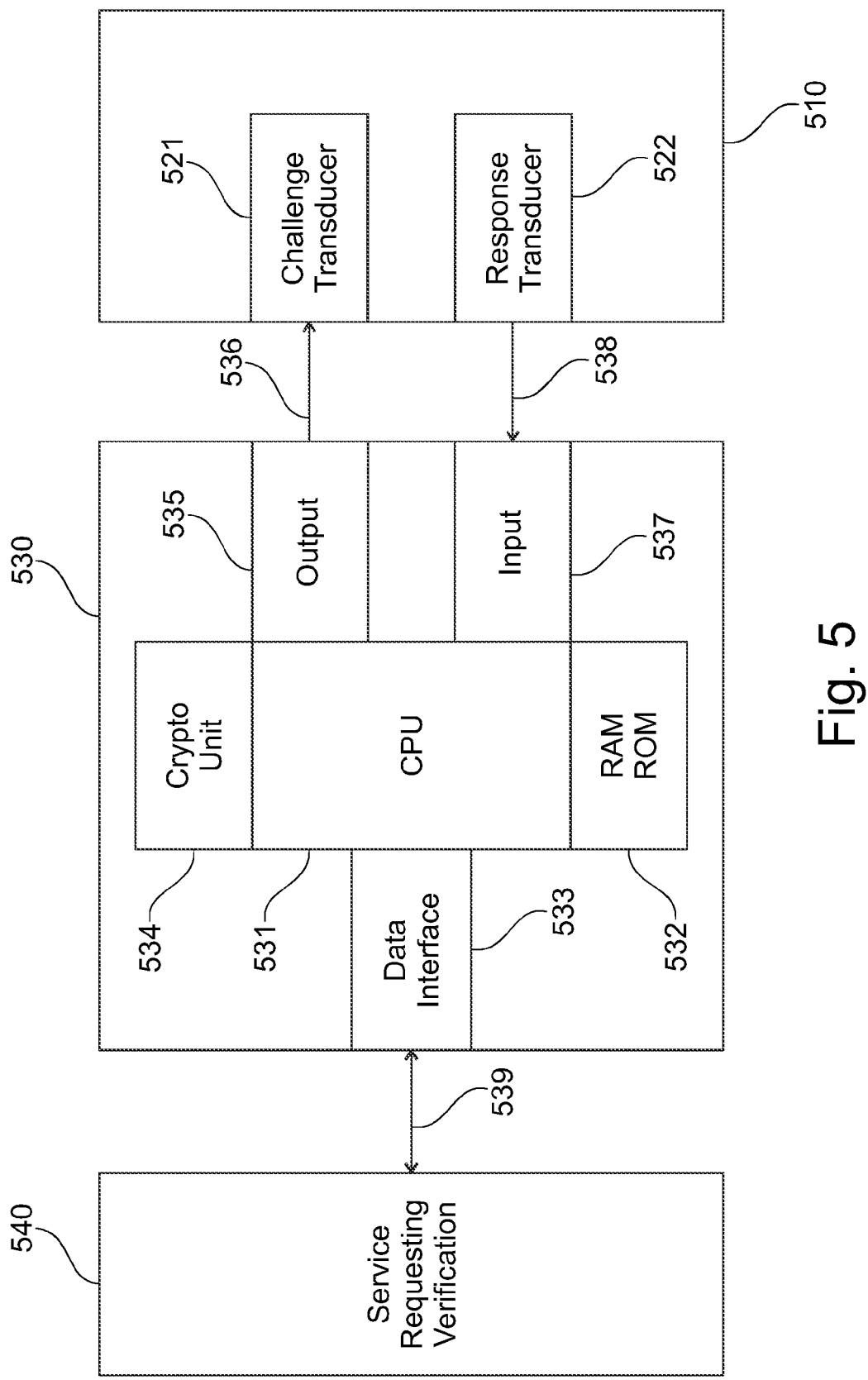
FIG. 5 shows a functional block diagram of a system according to an embodiment of the present invention.

FIG. 5 shows a functional block diagram of a system according to an embodiment of the present invention. More specifically, the system comprises apiece 510 of material having a transmitting (or challenge) transducer 521 and a receiving (or response) transducer 522 attached to an upper surface. Furthermore, the system comprises a signal processing unit 530 comprising a CPU 531, a memory unit 532, a data interface 533, a cryptography unit 534, an output interface 535, and an input interface 537. The data interface 533 is connected to a service device 540 via connection 539, the output interface 535 is connected to the transmitting transducer 521 via connection 536, and the input interface 537 is connected to the receiving transducer 522 via connection 522. Also in this embodiment, more than the two shown transducers 521 and 522 may be used as discussed above. The CPU 531 is adapted to communicate with the transducers 521 and 522 via the input interface 535 and output interface 537, respectively, such as to apply a predetermined stimulation to the piece 510 and to measure the corresponding response from the piece 5110. The data interface 533 is adapted to communicate with the service device 540 in order to receive an encrypted request from the service device 540 and to transmit an encrypted response to the service device 540. The cryptography unit 534 is adapted to decrypt the encrypted request received from the service device 540 and to generate the encrypted response to the service device 540. The operation of the system will be discussed in further detail below with reference to FIGS. 6 and 7.

Figure 6:
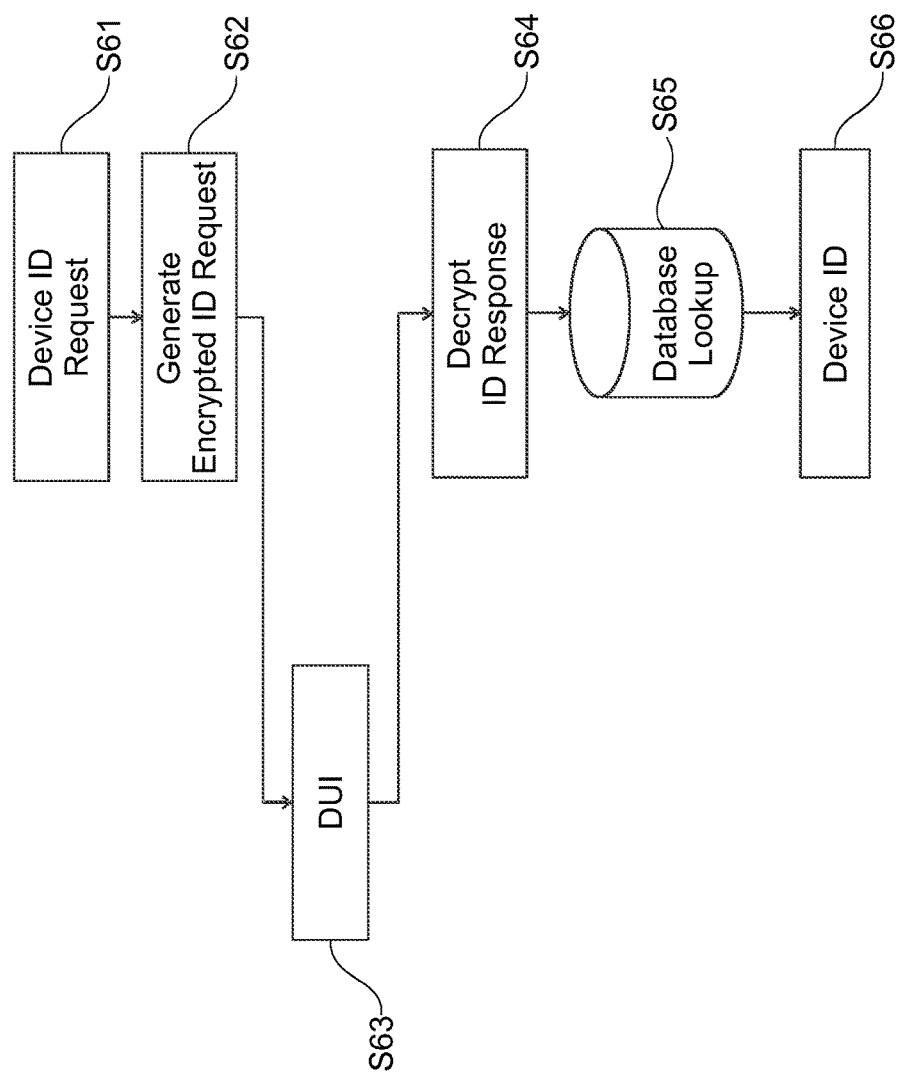
FIG. 6 is a flow diagram showing the general functioning of a system in accordance with an embodiment of the present invention.

FIG. 6 is a flow diagram showing the general functioning of a system in accordance with an embodiment of the present invention. More specifically, FIG. 6 illustrates the processing in the system shown in FIG. 5 and discussed above. The processing begins in step S61, where the service device 540 receives a request for obtaining the device ID of the asset (not shown) to which the piece 510 is irreversibly attached. Then, at step S62 the service device 540 generates an encrypted ID request and transmits it to the data interface 533 of the device under identification (DUI). At step S63, the DUI receives the encrypted request and processes it as described in further detail below with reference to FIG. 7. The result of the processing, i.e. data representative of one or more ultrasonic "fingerprints", is transmitted back to the service device 540 and decrypted at step S64. The decrypted "fingerprint(s)" is(are) provided as a query to a database in step S65 and the identified device ID is output in step S66.

Figure 7:
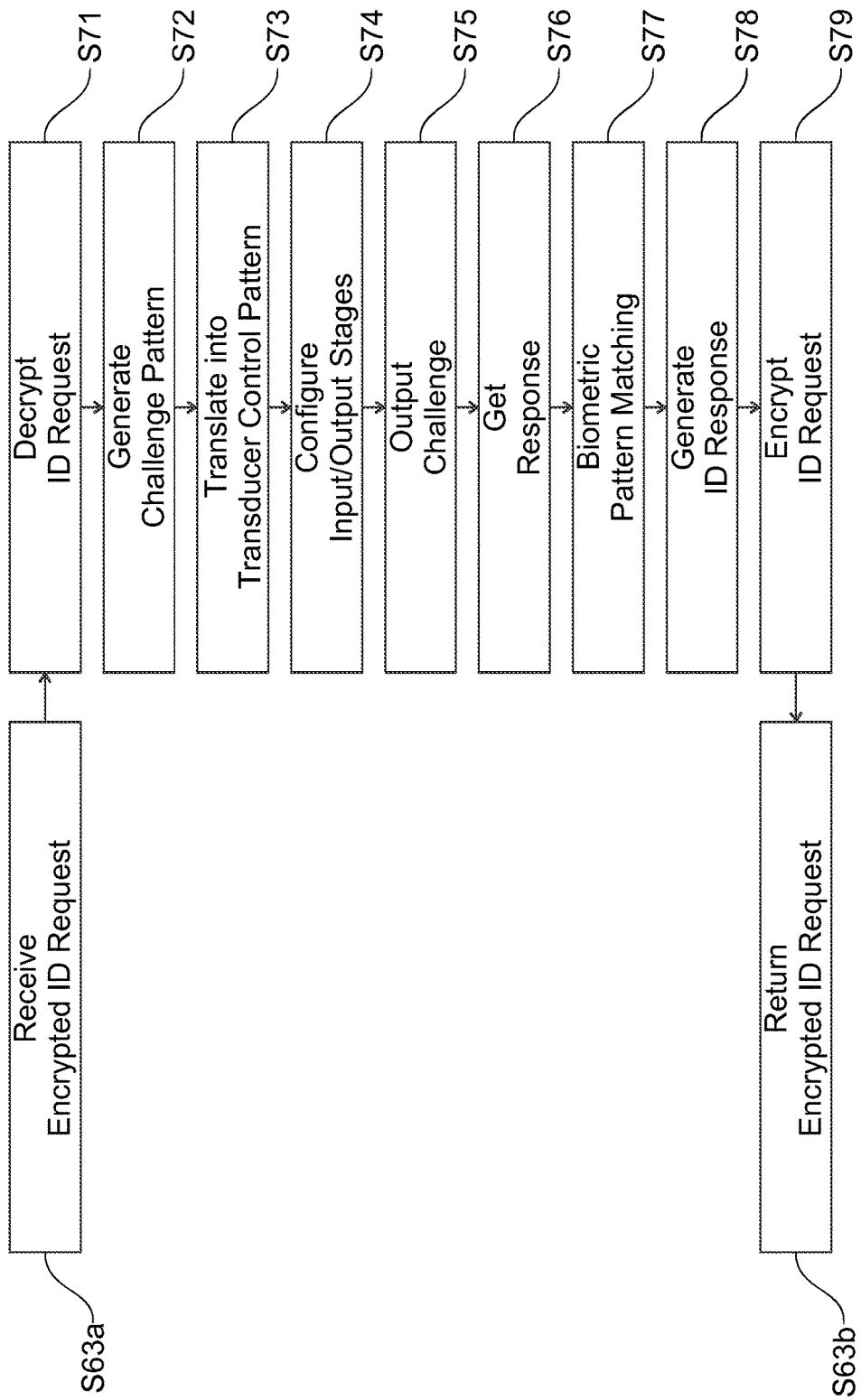
FIG. 7 is a flow diagram showing the detailed processing in step S63 of FIG. 6.

FIG. 7 is a flow diagram showing the detailed processing in step S63 of FIG. 6. More specifically, the processing begins at step S63a with receipt of the encrypted ID request from the service device 540. In step S71, the ID request is decrypted by the cryptographic unit 534. Then, based on information in the decrypted ID request or on information stored in the memory 532, a challenge pattern is generated at step S72. The challenge pattern identifies one or more transmission transducers 521 for stimulating the piece 510 and one or more receiving transducers 522 for measuring the response corresponding to the stimulation. The challenge pattern may further identify one or more frequencies to be used in the stimulation. In step S73, the received challenge pattern is translated into a transducer control pattern which can be applied by the CPU 531 through the interface 535 and 537. In step S74, the input and output stages (not shown) are configured as preparation for outputting the challenge stimulation. The latter is done in step S75 and the measured response is obtained in step S76. Based on the response, in particular on characteristic features extracted from the response, a biometric pattern matching is conducted at step S77 in order to determine whether the response resulting from the challenge stimulation corresponds with an expected response stored in a secure portion of the memory unit 532. The resulting ID response is generated at step S78 and encrypted at step S79 before it is returned to the service device 540 at step S63b.

Figure 8:
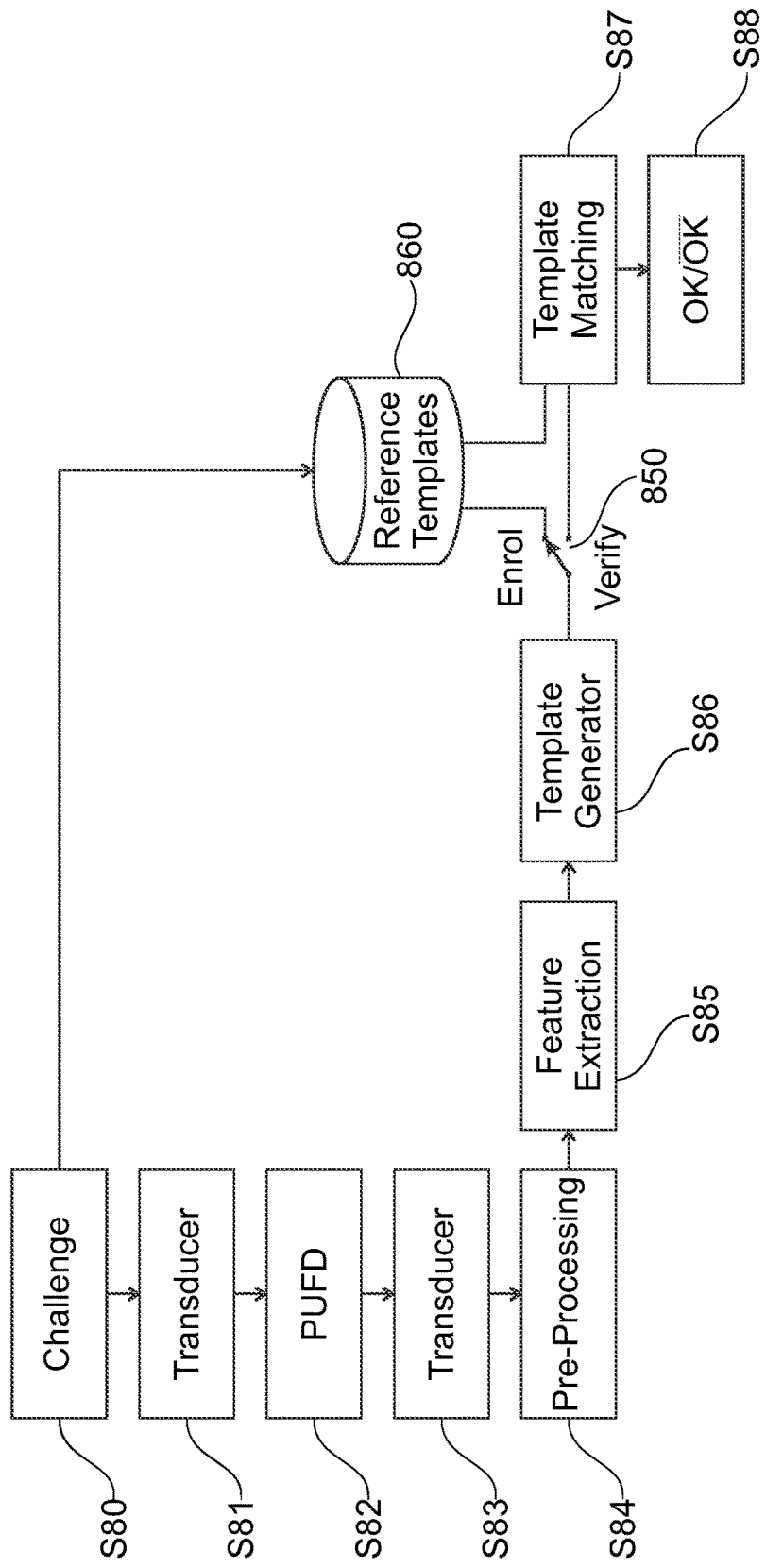
FIG. 8 is a combined block and flow diagram illustrating operation of a device in accordance with an embodiment of the present invention.

FIG. 8 is a combined block and flow diagram illustrating operation of a device in accordance with an embodiment of the present invention. The device comprises a switch 850 for switching between an enrolment mode and a verification mode. The switch 850 is shown in a position corresponding to the enrolment mode. In this mode, a particular challenge pattern is generated at step S80. The generated challenge pattern is stored in a secure part 860 of the memory unit 532 and forwarded to the transducers 521 and 522 for stimulating the piece 510 in accordance with the generated challenge pattern. In step S81, the transmitting transducer 521 applies the stimulation to the piece 510 (also denoted "physical unclonable function device (PUFD)) in step S81, the piece 510 responds in step S82, and the receiving transducer 522 receives the response in step S83 and forwards it for pre-processing by the CPU 531 in step S84. In step S85, the CPU 531 analyses the pre-processed response and extracts a number of characteristic features. In step S86, the CPU 531 generates a template based on the extracted features. The generated template is stored in the secure part 860 of the memory unit 532. These steps, i.e. S80 to S86, are repeated for all possible challenge patterns, i.e. for all possible combinations of transmitting and receiving reducers. Optionally, each challenge pattern may be applied using several different frequencies for the ultrasonic stimulation, such as 20 kHz, 40 kHz, 80 kHz, 160 kHz, 320 kHz, etc. Upon completion of the enrolment phase, the secure part 860 of the memory unit 532 contains at least one reference template for each challenge pattern.

Turning now to the verification mode, the steps S80 to S86 are performed in a similar way as in the enrolment mode described above. However, the verification mode differs from the enrolment mode in that the challenge at step S80 is generated in response to a received request for verification. The selected challenge pattern is marked in the secure part 860 of the memory unit 532 and the steps S81 to S86 are performed as described above. Then, the template generated at step S86 is input to a template matching step which also receives the marked reference template from the secure part 860 of the memory unit 532. Dependent on the outcome of the template matching step S87, the verification ends at step S88 with either an "OK" or a "not OK".

It is noted that, unless otherwise indicated, the use of terms such as "upper", "lower", "left", and "right" refers solely to the orientation of the corresponding drawing.

It is noted that the term "comprising" does not exclude other elements or steps and that the use of the articles "a" or "an" does not exclude a plurality. Also elements described in association with different embodiments may be combined. It should also be noted that reference signs in the claims should not be construed as limiting the scope of the claims.

The invention claimed is:

1. A device for identifying an asset, the device comprising
a piece of material having predetermined physical properties, the piece of material being adapted to be irreversibly attached to the asset,
a stimulation and measurement unit, including a plurality of stimulation elements, attached to the piece of material, the stimulation and measurement unit being adapted to apply a predetermined stimulation using sound waves to the piece of material and receive a corresponding response wirelessly from the piece of material and to measure the corresponding response, wherein the predetermined stimulation is applied using the plurality of stimulation elements affixed at different surfaces of the piece of material,
an analysis unit adapted to analyze the measured response from the piece of material, wherein the measured response corresponds to changes caused by physical properties of the piece of material in a signal transmitted by the predetermined stimulation, and
a communication unit adapted to output data representative of the analysis of the measured response.

2. The device according to claim 1, further comprising
a memory unit for storing an expected response corresponding to the predetermined stimulation,
wherein the analysis unit is adapted to determine whether the measured response from the piece of material corresponds to the expected response, and
wherein the communication unit is adapted to output data indicative of whether the measured response from the piece of material corresponds to the expected response.

3. The device according to claim 1, wherein the communication unit is adapted to output data representative of the measured response and/or of the expected response.

4. The device according to any of the preceding claims, further comprising a cryptographic unit adapted to decrypt an encrypted request for identification received by the communication unit and to encrypt data output by the communication unit.

5. The device according to claim 1, wherein the stimulation and measurement unit comprises a plurality of stimulation elements and a plurality of measurement elements.

6. The device according to claim 5, wherein
the plurality of stimulation elements are selected from the group consisting of acoustical stimulators, optical stimulators and electrical stimulators, and
The plurality of measurement elements are correspondingly selected from the group consisting of acoustical sensors, optical sensors and electrical sensors.

7. The device according to claim 5, wherein the stimulation elements comprise ultrasonic transducers for applying an ultrasonic stimulation to the piece of material, and wherein the measurement elements comprise ultrasonic transducers for measuring an ultrasonic response from the piece of material.

8. The device according to claim 5, wherein
the communication unit is adapted to receive a request for identification, the request for identification comprising a challenge identifying at least one of the plurality of stimulation elements and at least one of the plurality of measurement elements, and
the stimulation and measurement unit is adapted to apply the predetermined stimulation in accordance with the challenge by activating the at least one stimulation element identified by the challenge and to measure the corresponding response at the at least one measurement element identified by the challenge.

9. The device according to claim 1, wherein the stimulation and measurement unit is adapted to apply the predetermined stimulation as a signal having a predetermined frequency.

10. An asset comprising a device according to claim 1, wherein the piece of material is an integral part of the asset.

11. An identification system comprising:
an asset according to claim 1, and
a service device in data communication with the communication unit,
wherein the service device is adapted to transmit a request for identification to the communication unit and to receive data representative of the analysis of the measured response from the communication unit.

12. A method of identifying an asset to which a piece of material having predetermined physical properties is attached, the method comprising
wirelessly applying a predetermined stimulation using sound waves to the piece of material, wherein the piece of material responds to the predetermined stimulation by outputting an electrical response to the predetermined stimulation, wherein the predetermined electrical stimulation is applied using a plurality of stimulation elements affixed at different surfaces of the piece of material;
measuring the electrical response from the piece of material corresponding to the predetermined stimulation, wherein the measuring is performed by a processor including a response transducer;
analyzing, by the processor, the measured electrical response from the piece of material, wherein the measured response corresponds to changes caused by physical properties of the piece of material in a signal transmitted by the predetermined stimulation, and
outputting, by the processor, data representative of the analysis of the measured response.

13. The method according to claim 12, further comprising identifying the asset based on the data representative of the analysis of the measured response.

14. A non-transitory computer readable media comprising a computer program comprising computer executable instructions which, when executed by a computer, causes the computer to perform the method according to claim 12.

15. A device for identifying an asset, the device comprising
a piece of material having predetermined physical properties, the piece of material being adapted to be irreversibly attached to the asset,
a stimulation and measurement unit attached to the piece of material, the stimulation and measurement unit being adapted to apply a predetermined stimulation to the piece of material and receive a corresponding response wirelessly from the piece of material and to measure the corresponding response, wherein the applying of the predetermined stimulation includes using a plurality of signals of different frequencies that are applied in sequence, an analysis unit adapted to analyze the measured response from the piece of material, and a communication unit adapted to output data representative of the analysis of the measured response.

\* \* \* \* \*